US006780988B2

(12) United States Patent
Maeda et al.

(10) Patent No.: US 6,780,988 B2
(45) Date of Patent: Aug. 24, 2004

(54) PROCESSES FOR PRODUCING $P^1,P^4$-DIURIDINE-5'-TETRAPHOSPHATE (75) Inventors: Hideaki Maeda, Choshi (JP); Toshio Yamada, Choshi (JP); Hiroshi Sato, Choshi (JP); Yutaka Noda, Choshi (JP)

(73) Assignee: Yamasa Corporation, Choshi (JP)

( * ) Notice: Subject to any disclaimer, the term of this patent is extended or adjusted under 35 U.S.C. 154(b) by 104 days.

(21) Appl. No.: 10/120,367

(22) Filed: Apr. 12, 2002

(65) Prior Publication Data

US 2002/0156269 A1 Oct. 24, 2002

Related U.S. Application Data (63) Continuation of application No. 09/582,642, filed as application No. PCT/JP99/05415 on Oct. 1, 1999, now Pat. No. 6,458,964.

(30) Foreign Application Priority Data

Oct. 2, 1998 (JP) .......................................... 10/281663
Jun. 17, 1999 (JP) .......................................... 11/170681

(51) Int. Cl.[7] .............................................. C07H 21/02
(52) U.S. Cl. .................................. 536/26.21; 536/55.3
(58) Field of Search ............................. 536/26.21, 55.3; 544/243

(56) References Cited

U.S. PATENT DOCUMENTS 5,763,447 A     6/1998  Jacobus et al. .............. 514/265
6,319,908 B1 *  11/2001 Yerxa et al. ................... 514/51

FOREIGN PATENT DOCUMENTS

| HU | 216881 | 9/1999 |
| WO | WO-97/29756 A1 | 8/1997 |
| WO | WO-97/35591 A2 | 10/1997 |
| WO | WO-99/05155 A2 | 2/1999 |

OTHER PUBLICATIONS

Grant, R.L. et al, "Grant and Hackh's Chemical Dictionary", McGraw–Hill, New York, 1987, pp. 22–23.*
Pauling, Linus, General Chemistry, 2nd Ed.:, 1953, Freeman, San Francisco, P22 & 41.
Coste, H. et al., J. Biol. Chem., 262, 1987, 12096–12103.
Vallejo, C.G. et al, Biochimica et Biophysica Acta, 438, 1976, 304–309.

* cited by examiner

Primary Examiner—James O. Wilson
Assistant Examiner—Thomas McKenzie
(74) Attorney, Agent, or Firm—Oblon, Spivak, McClelland, Maier & Neustadt, P.C.

(57) ABSTRACT

The invention describes a process for producing $P^1,P^4$-di(uridine-5'-)tetraphosphate ($U_2P_4$) or a salt thereof from uridine 5'-monophosphate (UMP); wherein the process comprises at least one of the steps (a) and (b): (a) adding UMP diphenylphosphate (UMP-DPP) in divided portions during a step of reacting UMP-DPP with an organic alkali salt of pyrophosphate ($PP_i$) to produce a reaction mixture; wherein at least one equivalent of a first base is present during one portion of the reaction; (b) reacting UMP-DPP with a PPi-organic alkali salt in the presence of at least one equivalent of a second base to produce a reaction mixture, wherein the first base and the second base may be the same or different; (c) subsequently adding water to the reaction mixture to produce an aqueous reaction mixture; and optionally (d) adding an alkali to the aqueous reaction mixture.

30 Claims, 7 Drawing Sheets

PROCESSES FOR PRODUCING P¹,P⁴-DIURIDINE-5'-TETRAPHOSPHATE

This application is a Continuation of application Ser. No. 09/582,642 filed on Jul. 28, 2000, now U.S. Pat. No. 6,458,964. which was originally filed as International PCT application No. PCT/JP99/05415, filed Oct. 1, 1999.

FIELD OF THE INVENTION

The present invention relates to stable crystals of $P^1,P^4$-di(uridine 5'-)tetraphosphate ($U_2P_4$) or a salt thereof which are useful as an active ingredient of an expectorant or a therapeutic agent for pneumonia; a process for producing the crystals; and a process for efficiently producing $U_2P_4$ or a salt thereof.

BACKGROUND ART

A tetrasodium salt of $P^1,P^4$-di(uridine 5'-)tetraphosphate ($U_2P_4 \cdot 4Na$) represented by the following formula (I):

(I)

has an expectoration-inducing action and is a compound which is expected to be developed as an expectorant or a therapeutic agent for pneumonia (e.g., U.S. Pat. Nos. 5,789,391, 5,763,447, and 5,635,160).

Until now, $U_2P_4$ has not been obtained in crystal form, and has been prepared only in the form of a lyophilized product (see Example 1 of WO 99/05155). Typical $U_2P_4$ produced by conventional method has a purity as low as 90%, and contains by-products. Examples of by-products include nucleoside 5'-(poly)phosphates such as uridine 5'-tetraphosphate ($UP_4$), uridine 5'-triphosphate (UTP), uridine 5'-diphosphate (UDP), and uridine 5'-monophosphate (UMP); and dinucleoside polyphosphates such as $P^1,P^4$-di(uridine 5'-)triphosphate ($U_2P_3$) and $P^1,P^4$-di(uridine 5'-)diphosphate ($U_2P_2$). Particularly, it is difficult to separate nucleoside 5'-(poly)phosphates such as UTP from $U_2P_4$, and highly purified $U_2P_4$ has been produced only with great difficulty through a conventional purification method; i.e., ion-exchange chromatography (WO 99/05155, *Biochimica et Biophysica Acta*, 438, (1976) 304–309).

The above purified and lyophilized product has disadvantages such as high hygroscopicity. Therefore, preparation of a pharmaceutical from $U_2P_4$ must be carried out in a special apparatus in which moisture is well controlled. Even after preparation of a pharmaceutical, the product must be wrapped tightly. In addition, since the pharmaceutical has a very short available period due to poor stability of the lyophilized preparation, obtaining highly purified and stable $U_2P_4$ crystals has been desired.

$U_2P_4$ is synthesized from uridine 5'-monophosphate (UMP) by use of an activating agent such as diphenyl phosphorochloridate (DPC) and a phosphorylating agent such as a pyrophosphate (PPi). However, a conventional process provides a low synthesis yield; i.e., as low as approximately 10 wt. % (Example 4B of WO 99/05155), and can never serve as a practical process. Accordingly, development of a process for producing $U_2P_4$ at high yield and on a large scale has also been desired.

In view of the foregoing, an object of the present invention is to provide stable crystals of $U_2P_4$ or a salt thereof. Another object of the invention is to provide a process for producing the crystals. Still another object of the invention is to provide a process for efficiently producing $U_2P_4$ on a large scale.

DISCLOSURE OF THE INVENTION

The present inventors have conducted earnest studies on a method for purifying $U_2P_4$ and a process for synthesizing $U_2P_4$ from UMP. The inventors have found that $U_2P_4$ purified through anion exchange chromatography and chromatography using activated charcoal (activated-charcoal chromatography) can be easily crystallized and that use of specific reaction conditions has the effect of drastically increasing the yield of $U_2P_4$ in the synthesis of $U_2P_4$ or a salt thereof from UMP serving as a starting material and by use of DPC and PPi. The present invention has been achieved on the basis of these findings.

Accordingly, the present invention provides crystals of $P^1,P^4$-di(uridine 5'-)tetraphosphate or a salt thereof.

The present invention also provides a process for producing crystals of $P^1,P^4$-di(uridine 5'-)tetraphosphate or a salt thereof, which process comprises purifying crude $P^1,P^4$-di(uridine 5'-)tetraphosphate or a salt thereof through anion exchange chromatography and activated-charcoal chromatography and adding a hydrophilic organic solvent to a solution of purified $P^1,P^4$-di(uridine 5'-)tetraphosphate or a salt thereof, to thereby precipitate crystals.

The present invention also provides a process for producing $P^1,P^4$-di(uridine 5'-) tetraphosphate or a salt thereof from uridine 5'-monophosphate (UMP) serving as a starting material and by use of diphenyl phosphorochloridate (DPC) and a pyrophosphate (PPi), which process comprises at least one of the following treatment steps:

(a) adding UMP diphenylphosphate (UMP-DPP) in divided portions during a step of reaction of UMP-DPP with a PPi-organic alkali salt;

(b) carrying out a step of reaction of UMP-DPP with a PPi-organic alkali salt in the presence of a base; and (c) further treating the synthesized $U_2P_4$ with an alkali.

BEST MODE FOR CARRYING OUT THE INVENTION

The crystals of $U_2P_4$ or a salt thereof according to the present invention are obtained through purification of crude $U_2P_4$ or a salt thereof by use of specific means, and addition of a hydrophilic organic solvent to a solution of purified $U_2P_4$ or a salt thereof, to thereby precipitate the solute as crystals. The present invention will next be described in terms of (1) purification of $U_2P_4$ or a salt thereof and (2) crystallization of $U_2P_4$ or a salt thereof.

(1) Purification of $U_2P_4$ or a salt thereof $U_2P_4$ or a salt thereof can be purified through anion exchange chromatography and activated-charcoal chromatography performed in combination. Although the two chromatography techniques may be performed in arbitrary sequence, anion exchange chromatography preferably precedes activated-charcoal chromatography, in view of improvement of the purity of $U_2P_4$.

A styrenic or acrylic resin may be used as an anion-exchanging resin in the above-described chromatography techniques. Examples of resins which may be used include strongly basic anion-exchanging resins such as AMBERLITE IRA 402 (Rohm & Haas Co.), DIAION PA-312, and DIAION SA-11A (Mitsubishi Chemical Co. Ltd.), and weakly basic anion-exchanging resins such as AMBERLITE IRA 67 (Rohm & Haas Co.) and DIAION WA-30 (Mitsubishi Chemical Co. Ltd.).

The activated charcoal may be in the form of chromatography-grade activated charcoal which is crushed or shaped into particles, and may include commercially available products (e.g., those of Wako Pure Chemical Industries, Ltd. and Futamura Kagaku Kogyo).

Chromatography may be carried out in a batch manner, or by use of a column. When the column chromatography is carried out, an aqueous acid solution or a mixture thereof with a salt having enhanced ionic strength, such as sodium chloride, may be used as an eluent for anion exchange chromatography; and water or an aqueous solution of alkali such as sodium hydroxide may be used as an eluent for activated-charcoal column chromatography. A small-scale preliminary test may be conducted in order to appropriately determine the concentration of each eluent from the range of 0.001 M to 10 M.

(2) Crystallization of $U_2P_4$ or a salt thereof $U_2P_4$ or a salt thereof is crystallized through addition of an hydrophilic organic solvent to a solution containing the thus-purified $U_2P_4$ or a salt thereof.

Examples of the hydrophilic organic solvents which may be used include alcohols having six or fewer carbon atoms, such as methanol and ethanol; ketones such as acetone; ethers such as dioxane; nitrites such as acetonitrile; and amides such as dimethylformamide. Of these, alcohols, especially ethanol, are particularly preferred.

More specifically, a solution of the thus-purified $U_2P_4$ or a salt thereof, or a slurry obtained through concentration of the solution, is optionally treated to thereby adjust the pH to 6–9, and a hydrophilic organic solvent is added to the solution or slurry at 60° C. or less to thereby precipitate the solute as stable $U_2P_4$ crystals.

The thus-obtained $U_2P_4$ crystals of the present invention contain (1) $U_2P_4$ in an amount of 95% or more and (2) other homologous compounds in an amount of 5% or less.

In the present invention, other homologous compounds include nucleoside 5'-(poly)phosphates such as $UP_4$, UTP, UDP, and UMP; and dinucleoside polyphosphates such as $U_2P_3$ and $U_2P_2$.

More preferably, $U_2P_4$ crystals contain (1) $U_2P_4$ in an amount of 97% or more, (2) UDP in an amount of 1% or less, and (3) UTP in an amount of 1% or less. Particularly preferably, $U_2P_4$ crystals contain (1) $U_2P_4$ in an amount of 98% or more, (2) UDP in an amount of 0.5% or less, and (3) UTP in an amount of 0.5% or less.

Such highly purified $U_2P_4$ crystals may be in the form of a salt, hydrate, or hydrate salt. Examples of the salts include pharmaceutically acceptable salts such as alkali metal salts such as sodium salts and potassium salts; alkaline earth metal salts such as calcium salts and magnesium salts; and ammonium salts. The $U_2P_4$ may be substituted with 1–4 metal atoms to form a salt.

The above hydrate may comprise 3–8 molecules of water which are bound to or adhere to one molecule of $U_2P_4$, and the above hydrate salt may comprise 3–8 molecules of water which are bound to or adhere to one molecule of an alkali metal salt of $U_2P_4$.

Examples of preferred $U_2P_4$ crystals include $U_2P_4 \cdot 4Na$ crystals and hydrates thereof. Furthermore, the $U_2P_4 \cdot 4Na$ crystals are easy to handle and remarkably useful as compared with conventional lyophilized products, since the crystals are stable under high temperature, high humidity conditions and the water content of the crystals is stabilized at 5–15 wt. %, to thereby suppress further hygroscopicity.

As described above, the thus-obtained $U_2P_4 \cdot 4Na$ crystals of the present invention contain (1) $U_2P_4$ in an amount of 95% or more and (2) other homologous compounds in an amount of 5% or less. In addition, as described above, examples of the preferred $U_2P_4$ crystals include such crystals containing (1) $U_2P_4$ in an amount of 97% or more, (2) UDP in an amount of 1% or less, and (3) UTP in an amount of 1% or less, particularly crystals containing (1) $U_2P_4$ in an amount of 98% or more, (2) UDP in an amount of 0.5% or less, and (3) UTP in an amount of 0.5% or less.

Furthermore, the crystals of $U_2P_4$ or a salt thereof according to the present invention also include tautomers thereof.

The crystals of $U_2P_4$ or a salt thereof according to the present invention are optionally dried through a conventional method such as drying under reduced pressure, drying under air-flow, or drying by heating, and are subsequently placed in a container (e.g., bottle, pouch, can, ampoule). Packing in the container may be carried out such that the container is open, closed, airtight, or sealed. The open condition is not preferred, in view of maintenance of storage stability of the crystals.

Next, an efficient process for synthesizing $U_2P_4$ will be described.

Conventionally, $U_2P_4$ or a salt thereof has predominantly been synthesized from uridine 5'-monophosphate (UMP) serving as a starting material and by use of an activating agent such as diphenyl phosphorochloridate (DPC) and a phosphorylating agent such as a pyrophosphate (PPi). Specifically, DPC and tributylamine are added to a tributylamine salt of UMP, to thereby produce UMP diphenylphosphate (UMP-DPP) serving as a reactive intermediate, which is reacted with tributylamine pyrophosphate (TBA-PPi), to thereby obtain $U_2P_4$ or a salt thereof at a yield of approximately 9.6% (Example 4B of WO 99/05155).

The process according to the present invention is characterized in that at least one of the following treatment steps is carried out: (a) adding UMP-DPP in divided portions during a conventional step of reaction of UMP-DPP with a PPi-organic alkali salt; (b) carrying out reaction of UMP-DPP with a PPi-organic alkali salt in the presence of a base; and (c) further treating the synthesized $U_2P_4$ with an alkali. Two or more of the above treatment steps may be combined.

The step "(a) adding UMP-DPP in divided portions" refers to addition of UMP-DPP, which must be provided in an amount by mol of at least twice that of a PPi-organic alkali salt, in several portions rather than in a single portion. For example, a PPi-organic alkali salt is reacted with an equimol amount of UMP-DPP and the step is repeated. Although no particular limitation is imposed on the number of portions of UMP-DPP, 2–3 portions are preferred in view of increase of the yield.

Examples of the PPi-organic alkali salts include a hexylamine salt, a dibutylamine salt, a triethylamine salt, and a tributylamine salt. In reaction with UMP-DPP, the PPi-organic alkali salt may be dissolved in a solvent. Examples of the solvents include amides such as DMF, DMAC, and formamide; cyclic ethers such as dioxane and tetrahydrofuran; ketones such as acetone; and dimethylimidazolidinone, hexamethylphosphoric triamide, dimethylsulfoxide, acetonitrile, or a mixture of two or more of these. Subsequently, UMP-DPP is added to the solution, and the mixture is allowed to react at room temperature for approximately 30 minutes to five hours.

The step "(b) carrying out reaction of UMP-DPP with a PPi-organic alkali salt in the presence of a base" refers to a reaction carried out in the presence of a base. Examples of the bases include pyridine bases such as pyridine, 2,6-lutidine, 2,4-lutidine, 2,4,6-picoline, 2,4-dimethylaminopyridine, and 2,4,6-collidine, with pyridine being particularly preferred. A basic solvent for the reaction is also included in the bases used in the present invention. The concentration of the base is not particularly limited. The base is preferably added in an amount of 6 equivalents or more based on UMP, more preferably 18 equivalents or more.

Furthermore, the step "(c) further treating the synthesized $U_2P_4$ with an alkali" refers to quenching of a liquid containing synthesized $U_2P_4$ with waters and treating the mixture with a solution of an organic or inorganic alkali such as sodium hydroxide, ammonia, potassium hydroxide, pyridine, triethyalmine, or sodium carbonate. Conventionally, the quenched liquid as such is purified directly. However, the treatment with an alkali enables improvement of the isolation yield of $U_2P_4$ as compared with the conventional method.

In the treatment with an alkali, a liquid containing synthesized $U_2P_4$ is quenched with water, and an alkali is added to the mixture such that the pH of the mixture becomes approximately 8–13, preferably 10–12. The mixture is allowed to react at room temperature for approximately 10 minutes to five hours.

UMP-DPP can be synthesized from UMP through a conventional method. For example, a UMP trialkylamine salt such as a UMP tributylamine salt prepared through a conventional method is dissolved in a solvent. Examples of the solvents include amides such as DMF and dimethylacetamide (DMAC); cyclic ethers such as dioxane and tetrahydrofuran; ketones such as acetone; and dimethylimidazolidinone, hexamethylphosphoric triamide, or a mixture thereof. Subsequently, DPC and, if needed, a trialkylamine are added to the solution, and the mixture is allowed to react at room temperature for approximately 30 minutes to five hours, to thereby synthesize UMP-DPP serving as a reactive intermediate.

EXAMPLES

The present invention will next be described in more detail by way of examples.

Example 1

Synthesis of $U_2P_4$ or a Salt Thereof (1) Effect of a base

DMAC (8 mL) was added to a dehydrated uridine 5'-monophosphate tributylamine salt (UMP-TBA) (6.2 mmol), and DPC (1.7 mL) was added dropwise to the mixture with stirring. The thus-obtained mixture was reacted at room temperature for one hour to thereby form UMP-DPP, after which TBA (7.6 mL) was added to the reaction mixture, which was stirred for another 10 minutes. Meanwhile, dehydrated TEA-PPi (3.0 mmol) was dissolved in pyridine (1.7 mL), and the thus-prepared solution was added to the UMP-DPP reaction mixture. Subsequently, the mixture was stirred at room temperature for three hours, and water was added to the mixture to thereby stop the reaction. The obtained reaction mixture was analyzed by HPLC (at 262 nm), which showed that the target $U_2P_4$ was obtained at a yield of 18.3%.

As is apparent from the result, when UMP-DPP is reacted with TEA-PPi in the presence of a base (pyridine), $U_2P_4$ may be synthesized at about twice the yield obtained through a conventional method.

(2) Effect of combination use of base and alkali treatment

DMAC (8 mL) was added to a dehydrated uridine 5'-monophosphate tributylamine salt (UMP-TBA) (6.2 mmol), and DPC (1.7 mL) was added dropwise to the mixture with stirring. The thus-obtained mixture was reacted at room temperature for one hour to thereby form UMP-DPP, after which, TBA (7.6 mL) was added to the reaction mixture and the mixture was stirred for another 10 minutes. Meanwhile, dehydrated TEA-PPi (3.0 mmol) was dissolved in pyridine (1.7 mL), and the thus-prepared solution was added to the UMP-DPP reaction mixture. Subsequently, the mixture was stirred at room temperature for three hours, and water was added to the mixture to thereby stop the reaction. A 30% sodium hydroxide solution was added to the above-obtained reaction mixture so as to adjust pH to 11.0, and the mixture was allowed to stand overnight. The obtained reaction mixture was analyzed by HPLC (at 262 nm), which showed that the target $U_2P_4$ was obtained at a yield of 29.7%.

As is apparent from the result, when UMP-DPP is reacted with TEA-PPi in the presence of a base (pyridine) and further alkali treatment is performed, $U_2P_4$ may be synthesized at about three times the yield obtained through a conventional method.

(3) Effect of base and addition of UMP-DPP in several portions

Formamide (1.5 mL) and pyridine (1.5 mL) were added to a triethylamine salt of dehydrated pyrophosphoric acid (TEA-PPi) (6 mmol), and the mixture was stirred in a vessel. Meanwhile, in another vessel, DMAC (4.3 mL), dioxane (4.8 mL), and tributylamine (TBA) (5.8 mL) were added to a dehydrated uridine 5'-monophosphate tributylamine salt (UMP-TBA) (12 mmol), and the mixture was stirred. Subsequently, DPC (2.5 mL) was added dropwise to the mixture, and the thus-obtained mixture was further stirred at room temperature for one hour, to thereby form UMP-DPP. Half of the UMP-DPP reaction mixture was added dropwise to the vessel containing TEA-PPi, and reaction was allowed to proceed at room temperature for one hour. Subsequently, pyridine (1.5 mL) was added to the mixture, and the remaining UMP-DPP reaction mixture was added dropwise to the vessel. The thus-obtained reaction mixture was further reacted at room temperature for one hour, and water was added to the mixture to thereby stop the reaction. The obtained reaction mixture was analyzed by HPLC (at 262 nm), which showed that the target $U_2P_4$ was obtained at a yield of 29.5%.

As is apparent from the result, when UMP-DPP is added in two portions and UMP-DPP is reacted with TEA-PPi in the presence of a base (pyridine), $U_2P_4$ may be produced at about three times the yield obtained through a conventional method. As is also apparent from the result, addition of UMP-DPP in two portions provides a yield of 29.5%, which is about 1.6 times the yield obtained in (1) above (18.3%).

(4) Effect of alkali treatment

Formamide (1.5 mL) and pyridine (1.5 mL) were added to a triethylamine salt of dehydrated pyrophosphoric acid (TEA-PPi) (6 mmol), and the mixture was stirred in a vessel. Meanwhile, in another vessel, DMAC (4.3 mL), dioxane (4.8 mL), and tributylamine (TBA) (5.8 mL) were added to a dehydrated uridine 5'-monophosphate tributylamine salt (UMP-TBA) (12 mmol), and the mixture was stirred. Subsequently, DPC (2.5 mL) was added dropwise to the mixture, and the thus-obtained mixture was further stirred at room temperature for one hour, to thereby form UMP-DPP. Half of the UMP-DPP reaction mixture was added dropwise to the vessel containing TEA-PPi, and reaction was allowed to proceed at room temperature for one hour. Subsequently, pyridine (1.5 mL) was added to the mixture, and the remaining UMP-DPP reaction mixture was added dropwise to the vessel. The thus-obtained reaction mixture was further reacted at room temperature for one hour, and water was added to the mixture to thereby stop the reaction. A 30% Sodium hydroxide solution was added to the above-obtained reaction mixture so as to adjust pH to 11.0, and the mixture was allowed to stand overnight. The obtained reaction mixture was analyzed by HPLC (at 262 nm), which showed that the target $U_2P_4$ was obtained at a yield of 32.2%.

As is apparent from the result, when alkali treatment is added to the above-described (3), the yield is increased by about 10%; i.e., from 29.5% to 32.2%.

Example 2

Production of $U_2P_4$·4Na Crystals

Formamide (10 mL) and pyridine (15 mL) were added to a triethylamine salt of dehydrated pyrophosphoric acid (TEA-PPi) (40.5 mmol), and the mixture was stirred in a vessel. Meanwhile, in another vessel, DMAC (50 mL), dioxane (34 mL), and tributylamine (TBA) (30 mL) were added to a dehydrated uridine 5'-monophosphate tributylamine salt (UMP-TBA) (80 mmol), and the mixture was stirred. Subsequently, DPC (17.8 mL) was added dropwise to the mixture, and the thus-obtained mixture was further stirred at room temperature for one hour, to thereby form UMP-DPP. Half of the UMP-DPP reaction mixture was added dropwise to the vessel containing TEA-PPi, and reaction was allowed to proceed at room temperature for one hour. Subsequently, 4-dimethylaminopyridine (DMAP) (50 mg) and pyridine (15 mL) were added to the mixture, and the remaining UMP-DPP reaction mixture was added dropwise to the vessel. The thus-obtained reaction mixture was further reacted at room temperature for two hours, and water was added to the mixture to thereby stop the reaction. The reaction mixture was diluted with water to a total volume of 700 mL, and a sodium hydroxide solution was added to the solution to thereby adjust pH to 10. The solution was concentrated to 200 mL, and ethanol (250 mL) was added to the concentrated solution with stirring. The solution was allowed to stand at 4° C. overnight, and the supernatant was removed by decantation. The thus-obtained solution was diluted with water to a total volume of 250 mL, and was analyzed by HPLC (at 262 nm), which showed that the target $U_2P_4$ was obtained at a yield of 30.0%.

The above-obtained solution (110 mL) was diluted with water to a total volume of 2000 mL and the diluted solution was applied to a weak anion exchange column (AMBERLITE IRA-67) (Cl type) (200 mL). Subsequently, the column was washed with water, and by-products were eluted with 0.18 M hydrochloric acid, after which the target $U_2P_4$ was eluted with a 0.005 M hydrochloric acid solution containing 0.35 M NaCl (recovery percentage: 82.7%).

A sodium hydroxide solution was added to the thus-obtained eluate to thereby adjust pH to 2.5. Subsequently, the eluate was applied to an activated charcoal column (Taiko SGP), and the column was washed with water and eluted with a 0.05 M sodium hydroxide solution (recovery percentage: 84.9%).

The pH of the thus-obtained eluate was adjusted to 7.6, and the eluate was concentrated to 38 mL. Subsequently, ethanol (57 mL) was added to the concentrated solution to thereby obtain 3.1 g of $U_2P_4$·4Na crystals (water content: 7.8%) (isolation yield: 18.4%).

(Physical properties of $U_2P_4$·4Na crystals)

The $U_2P_4$·4Na crystals prepared in Example 2 were dried at 60° C. for four hours by use of a forced-air drier, and subjected to instrumental analysis. In addition, a lyophilized product of $U_2P_4$·4Na was prepared in the same way as in the method described in Example 1 of WO 99/05155, and the thus-prepared product was compared with the crystals in terms of physical properties.

(1) Instrumental analysis

1) Analysis of purity

The $U_2P_4$·4Na crystals obtained in Example 2, and fractions containing $U_2P_4$ after purification through each chromatography were subjected to analysis of purity by means of high performance liquid chromatography. The results are shown in Table 1. Conditions for the high performance liquid chromatography are described below.

Column: HITACHIGEL #3013-N (product of Hitachi Keisokuki Service)

Eluent: 10% $CH_3CN$, 0.18 M $NH_4Cl$, 0.03 M $KH_2PO_4$, and 0.03 M $K_2HPO_4$

Detection method: UV detection at 262 nm

TABLE 1

| $U_2P_4$ and its ana logues | Proportions of substances (wt. %) | | | |
|---|---|---|---|---|
| | Reaction mixture | After anion exchange column | After activated charcoal column | After crystallization |
| UMP | 7.5 | 0.5 | 0.3 | (−) |
| $U_2P_2$ | 29.8 | 0.4 | (−) | (−) |
| UDP | 2.5 | 0.1 | 0.2 | 0.1 |

TABLE 1-continued

| $U_2P_4$ and its analogues | Proportions of substances (wt. %) | | | |
|---|---|---|---|---|
| | Reaction mixture | After anion exchange column | After activated charcoal column | After crystallization |
| $U_2P_3$ | 17.6 | 0.2 | (–) | (–) |
| UTP | 13.0 | 0.8 | 0.4 | 0.1 |
| $U_2P_4$ | 21.0 | 97.9 | 98.6 | 99.8 |
| $UP_4$ | 7.3 | (–) | (–) | (–) |

(–): Below detectable limit

2) Water content

The $U_2P_4$·4Na crystals were subjected to measurement of water content by means of the Karl Fischer method, to thereby show a water content of 5–15 wt. %, which varied in accordance with the degree of drying. The results apparently show that three to eight water molecules bind or adhere to one $U_2P_4$ molecule.

3) Melting point

The $U_2P_4$·4Na crystals were subjected to measurement of melting point by means of a conventional method, to thereby provide a decomposition point of about 223° C. The decomposition point of the lyophilized product was about 220° C.

4) X-ray diffraction

Figure 1:
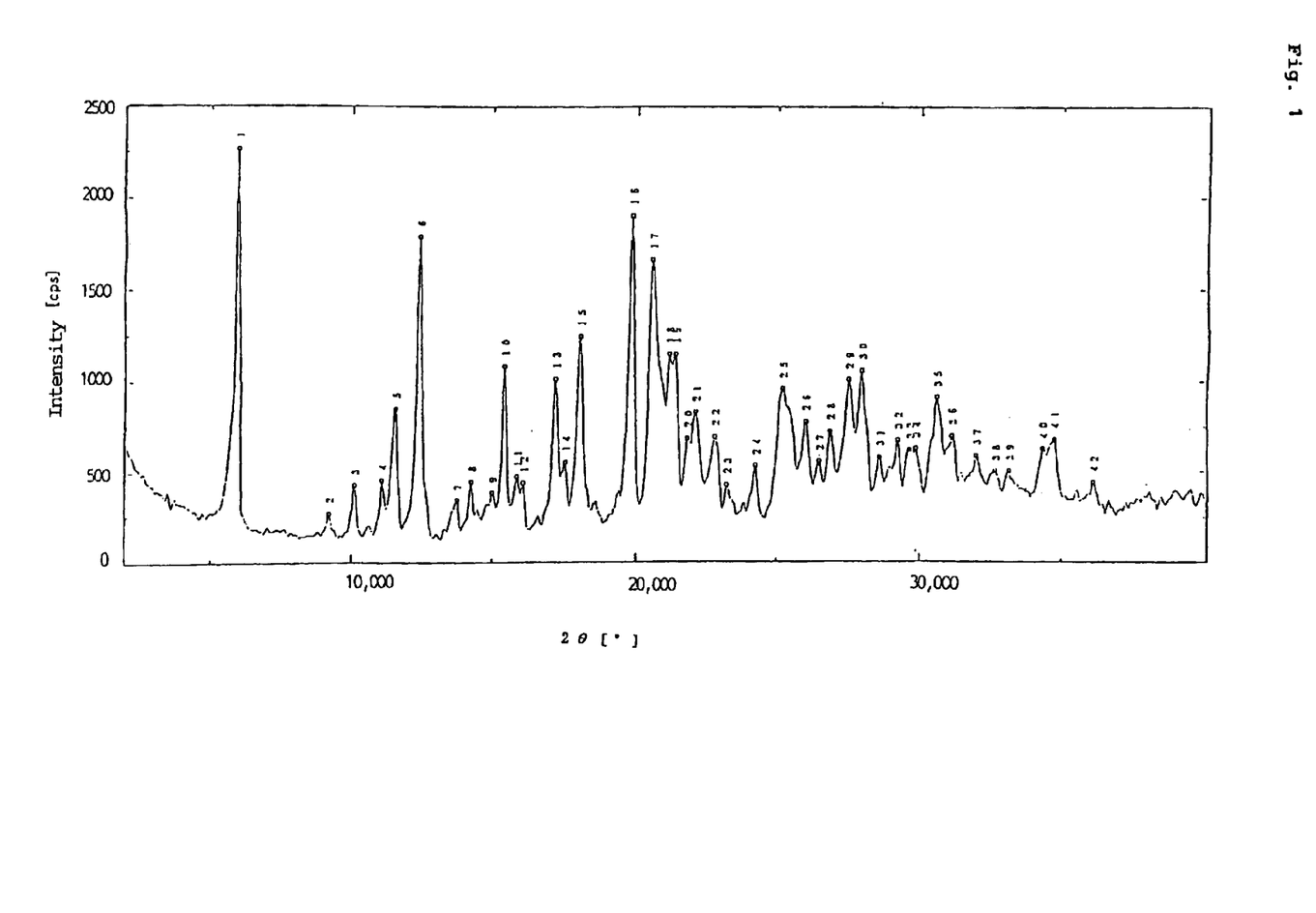
FIG. 1 shows an X-ray diffraction spectrum of a crystalline $U_2P_4 \cdot 4Na$ hydrate crystallized from ethanol solution.
Figure 2:
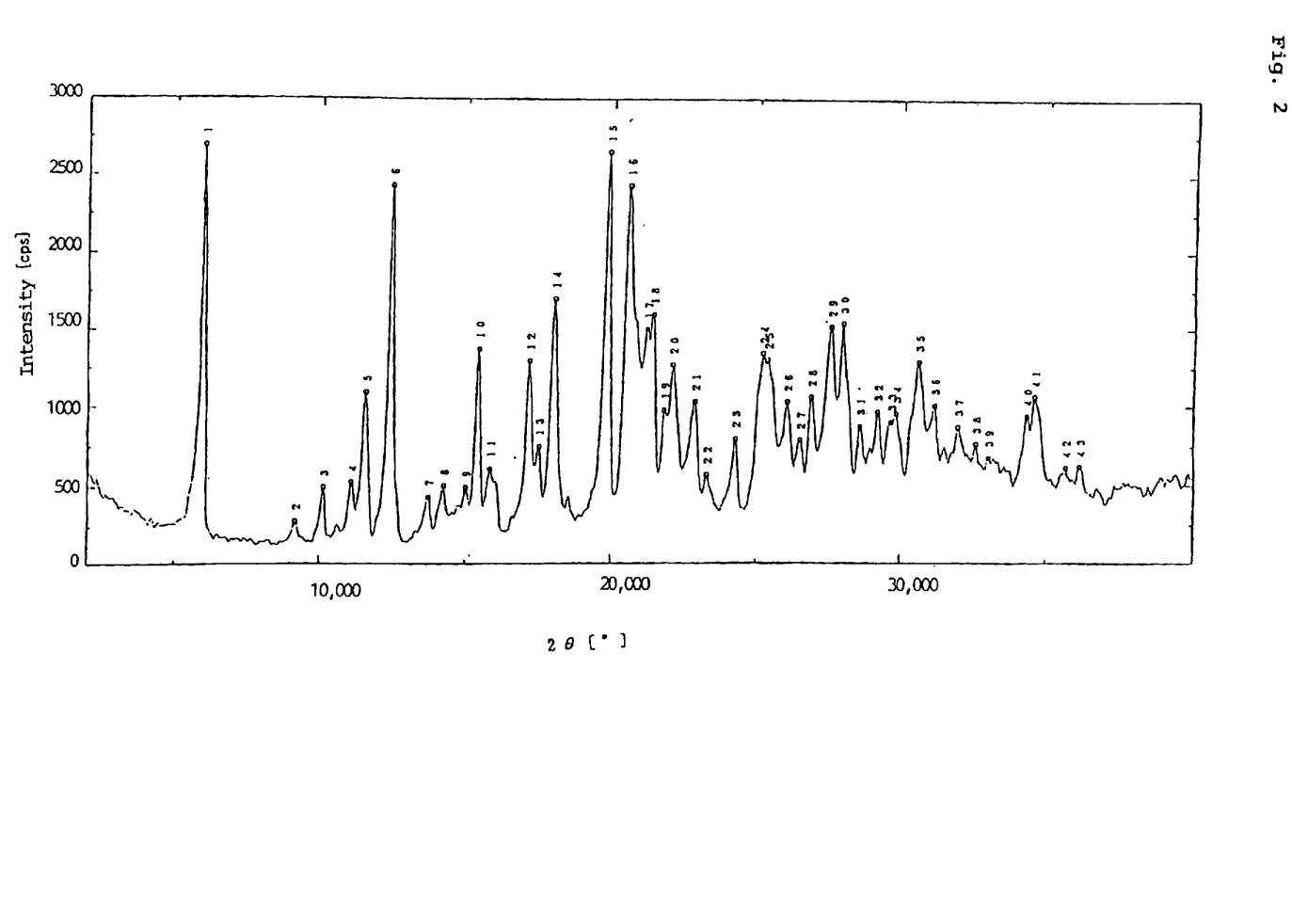
FIG. 2 shows an X-ray diffraction spectrum of crystalline $U_2P_4 \cdot 4Na$ octahydrate crystallized from ethanol solution.

The $U_2P_4$·4Na crystals were subjected to measurement of X-ray diffraction by use of an X-ray diffraction apparatus (Model; RINT2500V, product of Rigaku Denki) under the following conditions. The thus-obtained X-ray diffraction spectra are shown in FIGS. 1 and 2, and the peak data are shown in Tables 2 and 3.

(Conditions for measurement)

X-ray tube: Cu—Kα

X-ray output: 50 kV-300 mA

Scanning rate: 4.0°/minute

Scanning interval: 0.02°

Angle measuring range: 2–40°

Slit: DS-0.5°, RS-0.15 mm, SS-0.5°

Pre-treatment: Grinding by use of an agate mortar

TABLE 2

| Peak No. | 2θ (°) | Relative intensity ($I/I_0$) |
|---|---|---|
| 1 | 5.96 | 100 |
| 5 | 11.58 | 38 |
| 6 | 12.42 | 79 |
| 10 | 15.42 | 48 |
| 13 | 17.18 | 45 |
| 15 | 18.04 | 55 |
| 16 | 19.86 | 84 |
| 17 | 20.56 | 73 |
| 18 | 21.18 | 51 |
| 19 | 21.40 | 51 |
| 25 | 25.22 | 42 |
| 29 | 27.52 | 45 |
| 30 | 27.98 | 47 |
| 35 | 30.60 | 40 |

TABLE 3

| Peak No. | 2θ (°) | Relative intensity ($I/I_0$) |
|---|---|---|
| 1 | 5.96 | 100 |
| 5 | 11.56 | 41 |
| 6 | 12.42 | 90 |
| 10 | 15.42 | 51 |
| 12 | 17.18 | 48 |
| 14 | 18.04 | 63 |
| 15 | 19.86 | 90 |
| 16 | 20.58 | 90 |
| 17 | 21.20 | 56 |
| 18 | 21.42 | 59 |
| 24 | 25.20 | 50 |
| 29 | 27.54 | 56 |
| 30 | 27.96 | 57 |
| 35 | 30.60 | 48 |

Figure 3:
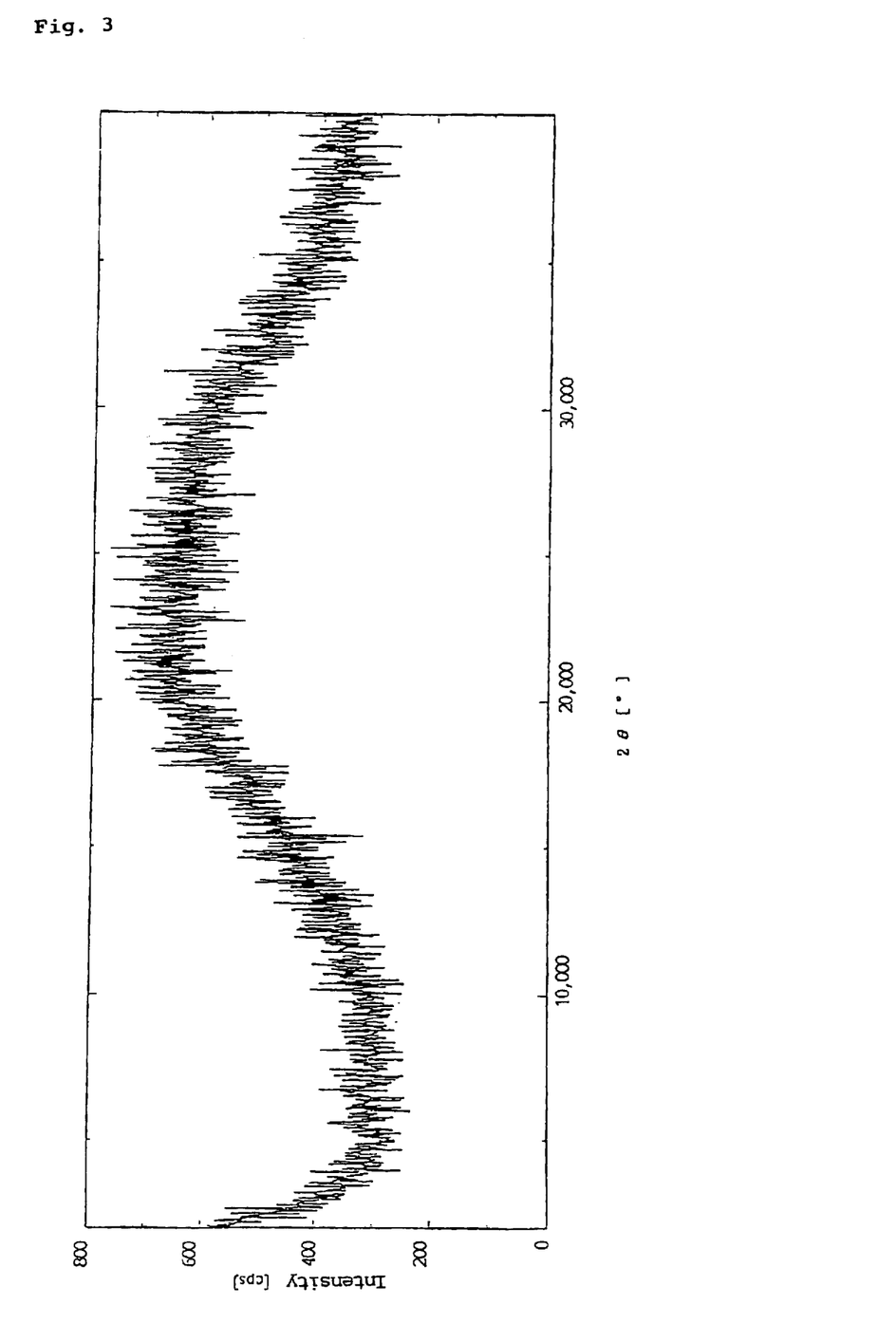
FIG. 3 shows an X-ray diffraction spectrum of $U_2P_4$ obtained through lyophilization.

FIG. 1 and Table 2 show the data for the crystals of $U_2P_4$·4Na tetrahydrate, and FIG. 2 and Table 3 show the data for the crystals of $U_2P_4$·4Na octahydrate. In addition, the X-ray diffraction spectrum of the lyophilized product is shown in FIG. 3 as a reference.

5) Hygroscopicity $U_2P_4$·4Na crystals (octahydrate) having a water content of approximately 14% were allowed to stand for nine days under the following conditions: a) 25° C. and a relative humidity of 57%; b) 25° C. and a relative humidity of 75%; and c) 40° C. and a relative humidity of 75%. No decomposition or change in weight was observed in the above three cases. The crystals have proven to be stable and to have no hygroscopicity. $U_2P_4$·4Na crystals (tetrahydrate) having a water content of approximately 8% were allowed to stand for nine days under conditions of 40° C. and a relative humidity of 75%. In this case, the water content increased to 14–15%. However, the water content did not increase further, and the crystals were stabilized.

In contrast, when a lyophilized product (initial water content: approximately 1%) was allowed to stand for nine days under conditions of 40° C. and a relative humidity of 75%, the water content increased gradually, and on the seventh day of storage the product assumed a mud-like state due to deliquescence.

6) Stability $U_2P_4$·4Na crystals (octahydrate) and a lyophilized product were placed in respective bottles, which were then sealed and allowed to stand for 13 days at 60° C. (acceleration test). No decomposition of the crystals was observed, while partial decomposition of the lyophilized product was confirmed through observation of a weight loss of $U_2P_4$·4Na of approximately 1.4%.

7) Crystal form

Figure 4:
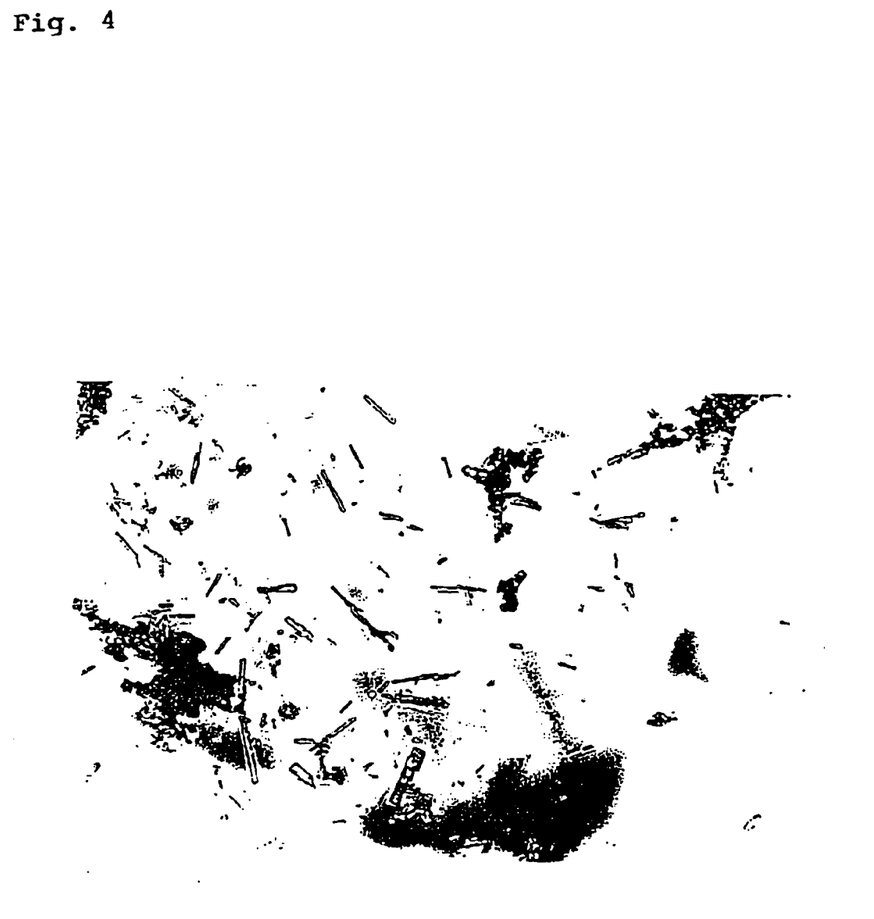
FIG. 4 is a photograph showing crystal form of crystalline $U_2 \cdot P4 \cdot 4Na$ octahydrate crystallized from ethanol solution. The photograph was taken under a polarizing microscope (magnification: 440), wherein 1 cm in the image corresponds to 23 $\mu$m.

FIG. 4 shows a photograph of a typical crystal form of $U_2P_4$·4Na (octahydrate) crystals.

8) IR absorption spectra

Figure 5:
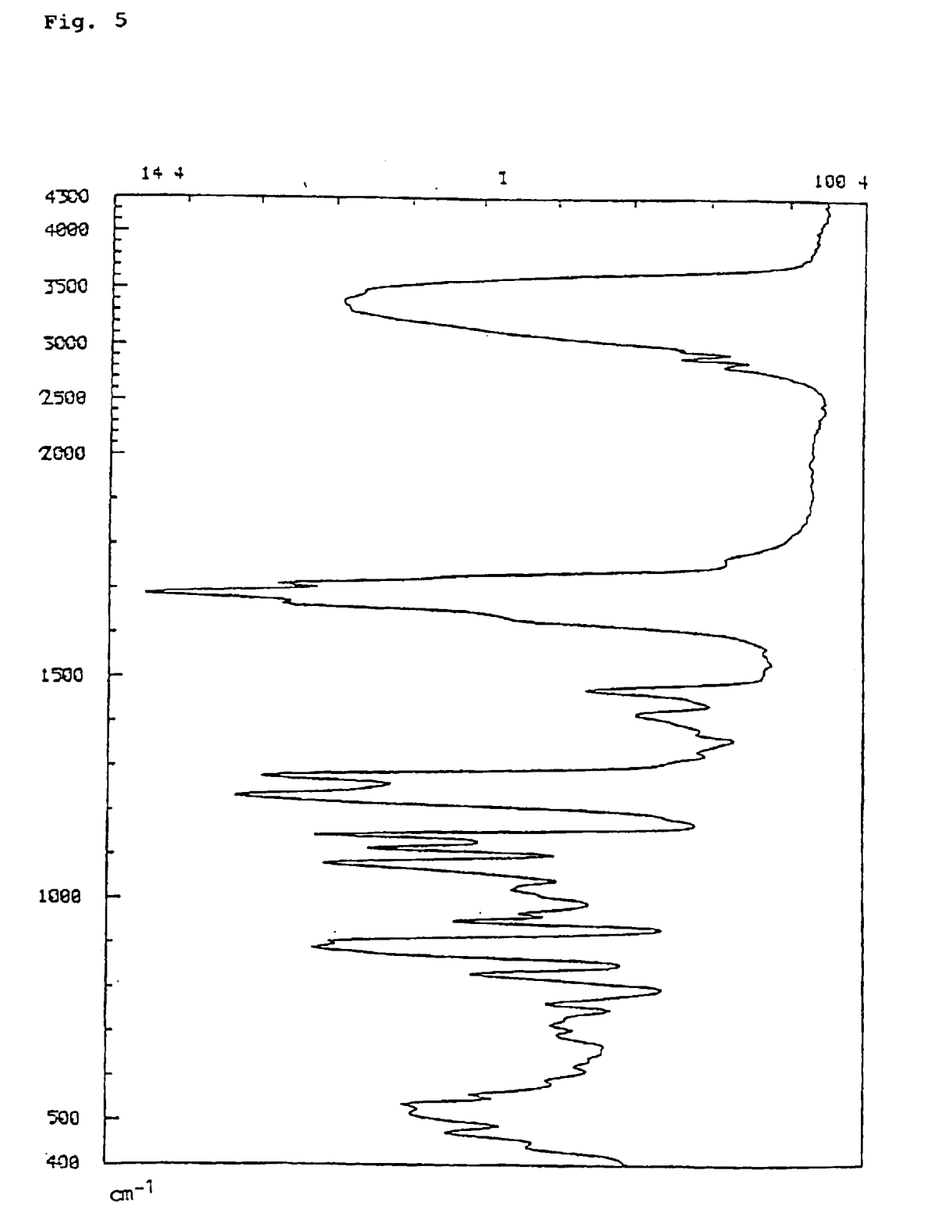
FIG. 5 shows an JR absorption spectrum of a $U_2P_4 \cdot 4Na$ hydrate crystallized from ethanol solution.
Figure 6:
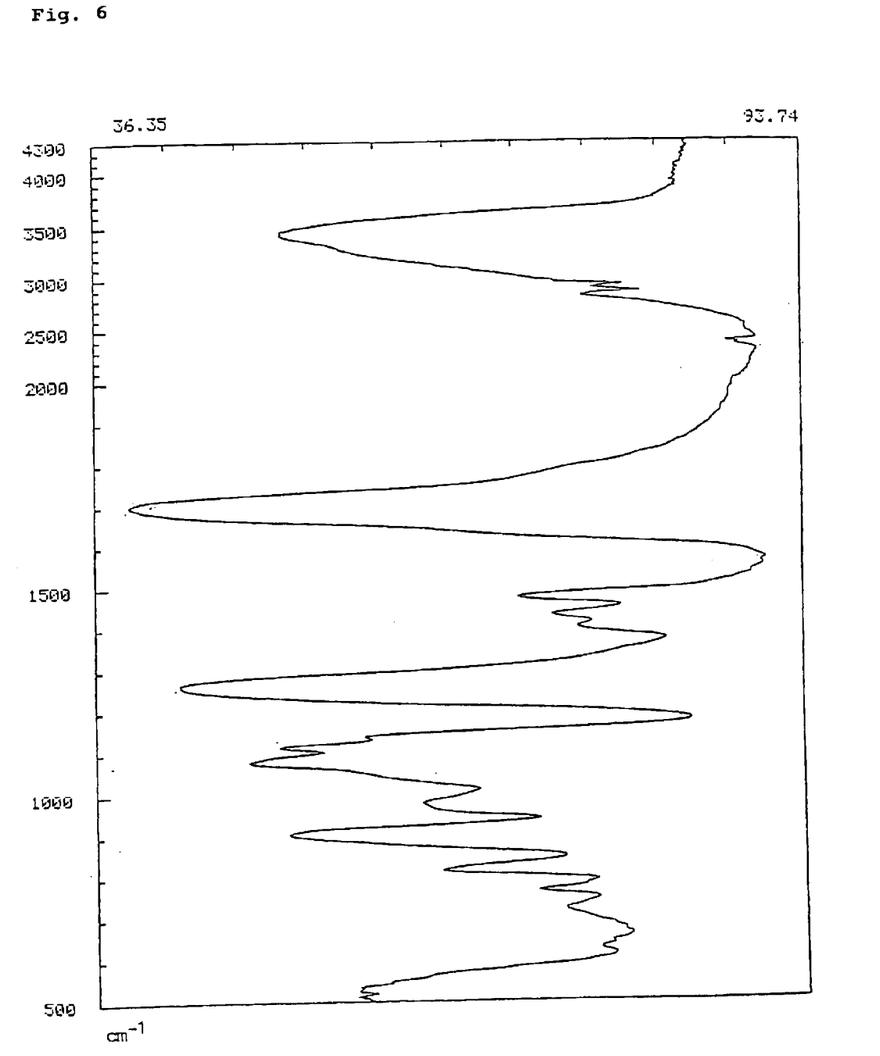
FIG. 6 shows an IR absorption spectrum of $U_2P_4$ obtained through lyophilization.

IR spectra of $U_2P_4$·4Na crystals (octahydrate) and a lyophilized product were measured in a customary manner by use of a JASCO 5000 Spectrophotometer. The results are shown in FIGS. 5 and 6. The lyophilized product of $U_2P_4$·4Na exhibits peaks at 3416, 1702, 1266, 1116, 1079, and 906 (cm$^{-1}$) (FIG. 6), whereas $U_2P_4$·4Na crystals exhibit peaks at 3386, 1690, 1277, 1233, 1146, 1116, and 890 (cm$^{-1}$) (FIG. 5).

Example 3

Production of $U_2P_4$·4Na Octahydrate Crystals

The fraction containing $U_2P_4$ obtained through treatment with a column in Example 2 was concentrated to thereby prepare a slurry, and pH thereof was adjusted to 7.0. Methanol was gradually added to the slurry with stirring, and the slurry was further stirred with cooling to 10° C., to thereby precipitate $U_2P_4 \cdot 4Na$ crystals.

Figure 7:
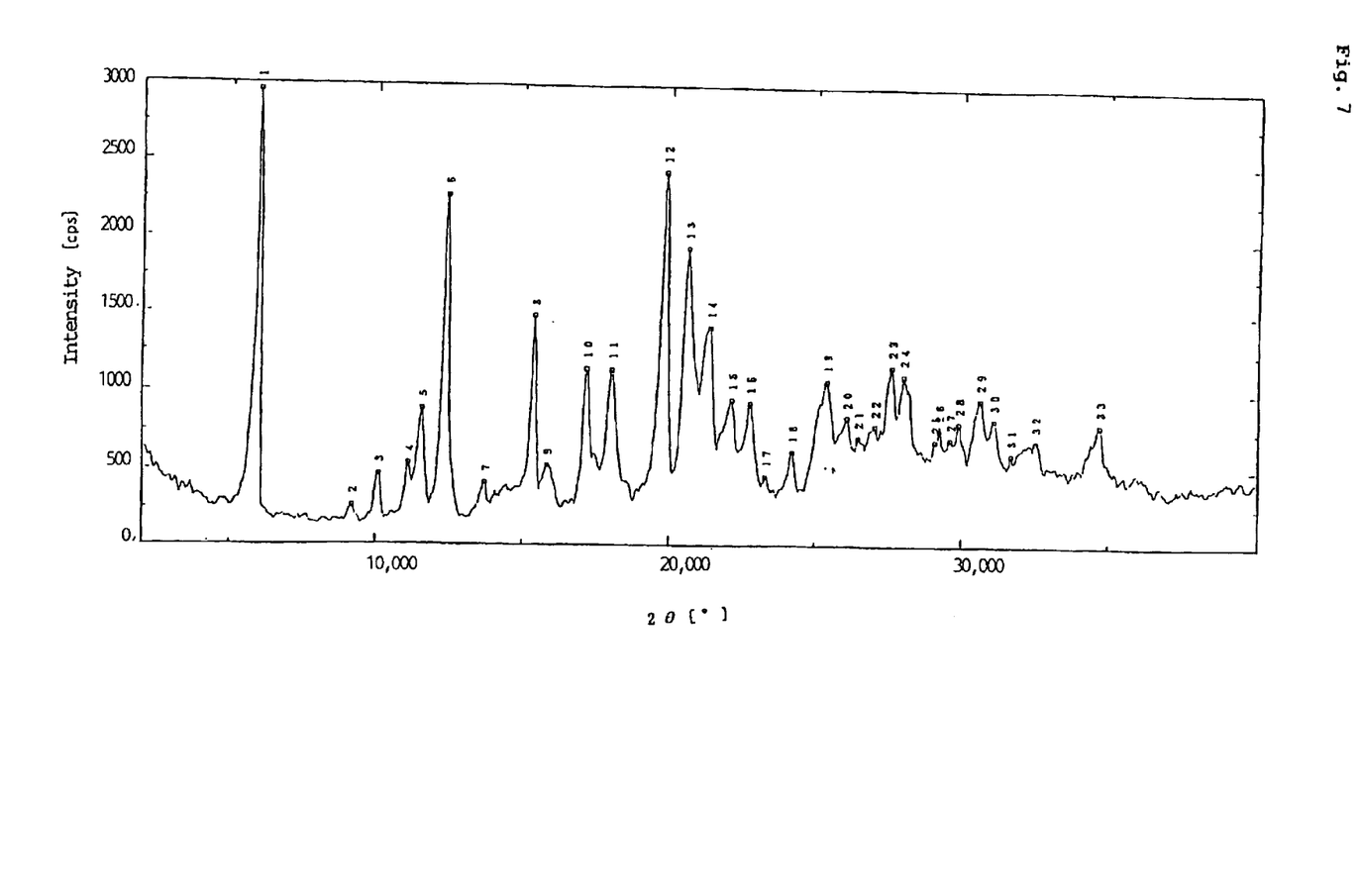
FIG. 7 shows an X-ray diffraction spectrum of crystalline $U_2P_4 \cdot 4Na$ octahydrate crystallized from methanol solution.

The water content of the thus-obtained and dried $U_2P_4 \cdot 4Na$ crystals was measured through the Karl Fischer method, to thereby determine that the crystals are octahydrate. The X-ray diffraction spectrum of the crystals is shown in FIG. 7, and peak data thereof are shown in Table 4.

TABLE 4

| Peak No. | 2θ (°) | Relative intensity (I/I₀) |
|---|---|---|
| 1 | 5.96 | 100 |
| 5 | 11.58 | 30 |
| 6 | 12.42 | 77 |
| 8 | 15.40 | 50 |
| 10 | 17.20 | 38 |
| 11 | 18.04 | 38 |
| 12 | 19.84 | 82 |
| 13 | 20.62 | 66 |
| 14 | 21.42 | 48 |
| 19 | 25.38 | 36 |
| 25 | 27.58 | 39 |
| 24 | 27.98 | 37 |
| 30 | 30.64 | 33 |

Industrial Applicability

As described hereinabove, the crystals of $U_2P_4$ or a salt thereof obtained through the process according to the present invention have high purity and stability and less hygroscopicity as compared with a lyophilized product, to thereby serve as a useful raw material for preparing a pharmaceutical.

The process for producing $U_2P_4$ or a salt thereof according to the present invention realizes high yield and enables large-scale synthesis.

What is claimed is:

1. A process for producing $P^1,P^4$-di(uridine 5'-)tetraphosphate ($U_2P_4$) or a salt thereof from uridine 5'-monophosphate (UMP) by reacting UMP with diphenyl phosphorochloridate (DPC) and a pyrophosphate (PPi), which process comprises steps (a) or (b); or both (a) and (b); and (c); and optionally (d); wherein the steps are described as follows:
    (a) adding UMP diphenylphosphate (UMP-DPP) in divided portions during a step of reacting UMP-DPP with a PPi-organic alkali salt to produce a reaction mixture; wherein at least one equivalent of a first base is present during one portion of the reaction;
    (b) reacting UMP-DPP with a PPi-organic alkali salt in the presence of at least one equivalent of a second base to produce a reaction mixture;
    wherein the first base and the second base may be the same or different;
    (c) adding water to the reaction mixture to produce an aqueous reaction mixture; and
    (d) adding an alkali to the aqueous reaction mixture.

2. The process for producing $P^1,P^4$-di(uridine 5'-)tetraphosphate ($U_2P_4$) or a salt thereof according to claim 1, comprising each of steps (a) to (d).

3. The process of claim 2, wherein at least one base is selected from the group consisting of pyridine, 2,6-lutidine, 2,4-lutidine, 2,4,6-picoline, 2,4-dimethylaminopyridine, and 2,4,6-collidine.

4. The process of claim 1, comprising steps (a), (b), and (c).

5. The process of claim 4, wherein said first base and second base are selected from the group consisting of pyridine, 2,6-lutidine, 2,4-lutidine, 2,4,6-picoline, 2,4-dimethylaminopyridine, and 2,4,6-collidine.

6. The process of claim 1, comprising steps (a), (c), and (d).

7. The process of claim 6, wherein said alkali is selected from the group consisting of sodium hydroxide, ammonia, potassium hydroxide, pyridine, triethylamine, and sodium carbonate.

8. The process of claim 6, wherein said first base is selected from the group consisting of pyridine, 2,6-lutidine, 2,4-lutidine, 2,4,6-picoline, 2,4-dimethylaminopyridine, and 2,4,6-collidine.

9. The process of claim 1, comprising steps (b), (c), and (d).

10. The process of claim 9, wherein said second base is selected from the group consisting of pyridine, 2,6-lutidine, 2,4-lutidine, 2,4,6-picoline, 2,4-dimethylaminopyridine, and 2,4,6-collidine.

11. The process of claim 9, wherein said alkali is selected from the group consisting of sodium hydroxide, ammonia, potassium hydroxide, pyridine, triethylamine, and sodium carbonate.

12. The process of claim 1, further comprising purifying the $U_2P_4$ by anion exchange chromatography.

13. The process of claim 1, further comprising purifying the $U_2P_4$ by activated-charcoal chromatography.

14. The process of claim 1, further comprising purifying the $U_2P_4$ by anion exchange chromatography and activated-charcoal chromatography.

15. The process of claim 1, wherein said process comprises step (b), and said second base is selected from the group consisting of pyridine, 2,6-lutidine, 2,4-lutidine, 2,4,6-picoline, 2,4-dimethylaminopyridine, and 2,4,6-collidine.

16. The process of claim 1, wherein said process comprises step (d), and said alkali comprises a solution of an organic or inorganic base.

17. The process of claim 1, wherein said process comprises step (d), and said alkali is selected from the group consisting of sodium hydroxide, ammonia, potassium hydroxide, pyridine, triethylamine, and sodium carbonate.

18. The process of claim 1, wherein said process comprises step (d), wherein the aqueous reaction mixture has a pH of 8–13.

19. The process of claim 1, wherein said process comprises step (d), wherein the aqueous reaction mixture has a pH of 10–12.

20. The process of claim 1, wherein said process comprises step (a), and the PPi-organic alkali salt is selected from the group consisting of hexylamine salts of PPi, dibutylamine salts of PPi, triethylamine salts of PPi, and tributylamine salts of PPi.

21. The process of claim 1, wherein said reacting is carried out in the presence of at least one solvent.

22. The process of claim 21, wherein the solvent is selected from the group consisting of DMF, DMAC, formamide, cyclic ethers, dioxane, tetrahydrofuran, ketones, acetone, dimethylimidazolidinone, hexamethylphosphoric triamide, dimethylsulfoxide, acetonitrile, and mixtures thereof.

23. The process of claim 1, comprising steps (a) and (c).

24. The process of claim 23, wherein said first base is selected from the group consisting of pyridine, 2,6-lutidine, 2,4-lutidine, 2,4,6-picoline, 2,4-dimethylaminopyridine, and 2,4,6-collidine.

25. The process of claim 1, comprising steps (b) and (c).

26. The process of claim 25, wherein said second base is selected from the group consisting of pyridine, 2,6-lutidine, 2,4-lutidine, 2,4,6-picoline, 2,4-dimethylaminopyridine, and 2,4,6-collidine.

27. The process of claim 1, wherein said process comprises step (b), and the PPi-organic alkali salt is selected from the group consisting of hexylamine salts of PPi, dibutylamine salts of PPi, triethylamine salts of PPi, and tributylamine salts of PPi.

28. The process of claim 1, wherein said process comprises step (a) or (b) or both steps (a) and (b) and the PPi-organic alkali salt employed in each step may be the same or different and is selected from the group consisting of hexylamine salts of PPi, dibutylamine salts of PPi, triethylamine salts of PPi, and tributylamine salts of PPi.

29. The process of claim 1, wherein said first base or said second base is present in an amount of at least 6 equivalents based on UMP.

30. The process of claim 1, wherein said first base or said second base is present in an amount of at least 18 equivalents based on UMP.

* * * * *

UNITED STATES PATENT AND TRADEMARK OFFICE
CERTIFICATE OF CORRECTION

PATENT NO. : 6,780,988 B2
DATED : August 24, 2004
INVENTOR(S) : Maeda et al.

It is certified that error appears in the above-identified patent and that said Letters Patent is hereby corrected as shown below:

<u>Title page,</u>
Item [75], Inventors, the 4th inventor should be deleted. It should read:

-- [75] Inventors: Hideaki Maeda, Choshi (JP); Toshio Yamada, Choshi (JP); Hiroshi Sato, Choshi (JP) --

<u>Column 11,</u>
Line 42, "UMIP" should read -- UMP --.

Signed and Sealed this

Thirtieth Day of November, 2004

JON W. DUDAS
*Director of the United States Patent and Trademark Office*